United States Patent [19]

Meisinger

[11] 4,120,687
[45] Oct. 17, 1978

[54] BENZOPHENONES AND BENZHYDROLS

[76] Inventor: Robert H. Meisinger, 1005 Gerson Dr., Warminster, Pa. 18974

[21] Appl. No.: 659,609

[22] Filed: Feb. 19, 1976

[51] Int. Cl.$^2$ .............................................. A01N 5/00
[52] U.S. Cl. ................................. 71/78; 71/91; 71/92; 71/98; 71/105; 71/108; 71/113; 71/116; 71/118; 71/121; 71/122; 71/123; 71/DIG. 1
[58] Field of Search .................................. 71/78, 123

[56] References Cited

U.S. PATENT DOCUMENTS

| | | | |
|---|---|---|---|
| 2,671,016 | 3/1954 | Erickson et al. | 71/123 |
| 3,013,079 | 12/1961 | Pearson | 71/123 |
| 3,193,373 | 7/1965 | Parups | 71/78 |
| 3,443,928 | 5/1969 | Batchelor | 71/78 |
| 3,853,532 | 12/1974 | Rein et al. | 71/78 |
| 3,898,275 | 8/1975 | Houlihan | 71/123 |
| 3,954,875 | 5/1976 | Swithenbank et al. | 71/123 |

FOREIGN PATENT DOCUMENTS 579,090  7/1959  Canada ......................... 71/78

OTHER PUBLICATIONS

Yu et al., "Tetraacyloxysilanes in Organic Synthesis, etc.," (1959), CA 54 pp. 20824–20825 (1960).

*Primary Examiner*—Glennon H. Hollrah
*Attorney, Agent, or Firm*—William E. Lambert, III

[57] ABSTRACT

Compounds having the formula

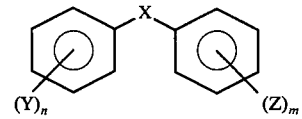

where
  X is —CO— or —CHOH—,
  Y and Z are halogen, alkyl, trifluoromethyl, alkoxy, hydroxy, nitro, cyano, carboxy, carbalkoxy, carbamoyl, or alkylthio, and
  m and n are 0, 1, or 2 are useful in controlling undesirable secondary growth in plants, particularly sucker growth in tobacco.

6 Claims, No Drawings

BENZOPHENONES AND BENZHYDROLS

This invention relates to plant growth control, and more particularly to control of the undesirable growth of suckers in tobacco plants.

Various plants, including tobacco and tomato, are subject to various forms of undesirable secondary growth. For example, in tobacco, the growth of suckers, that is axillary buds, not only detracts from the growth of the tobacco leaves, but also has a deleterious effect on the quality of the tobacco produced from the leaves. Manual removal of these suckers is both time-consuming and expensive. Furthermore, many of the chemicals heretofore employed in removing these suckers have been too expensive or have caused unwanted side effects.

It has now been found that sucker growth in tobacco plants can be controlled by applying to the growing plants a benzophenone or a benzhydrol. Generally, the compounds which are useful in inhibiting tobacco sucker growth have the formula

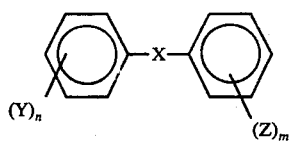

(I)

wherein

X is a group of the formula —CO— or —CHOH—, each Y independently is a halogen atom, preferably a chlorine or a bromine atom, an alkyl group, preferably having up to 8 carbon atoms, most preferably a methyl group, a trifluoromethyl group, an alkoxy group, preferably having up to 4 carbon atoms, a hydroxy group, a nitro group, a cyano group, a carboxy group, a carbalkoxy group, preferably having up to 4 carbon atoms in the alkoxy moiety, a carbamoyl group, an alkyl or dialkyl carbamoyl group, preferably having up to 4 carbon atoms in the alkyl groups, or an alkylthio group, preferably having up to 4 carbon atoms;

each Z independently is a halogen atom, preferably a chlorine or a bromine atom, an alkyl group, preferably having up to 8 carbon atoms, most preferably a methyl group, a trifluoromethyl group, an alkoxy group, preferably having up to 4 carbon atoms, a hydroxy group, a nitro group, a cyano group, a carboxy group, a carbalkoxy group, preferably having up to 4 carbon atoms in the alkoxy moiety, a carbamoyl group, an alkyl or dialkyl carbamoyl group, preferably having up to 4 carbon atoms in the alkyl groups, or an alkylthio group, preferably having up to 4 carbon atoms;

$m$ is 0, 1, 2, preferably 0 or 1; and $n$ is 0, 1, 2, or 3, preferably 1 or 2.

A preferred group of benzophenones and benzhydrols which are useful in the present invention are those in which the Y and Z substituents are halogen atoms or alkyl groups, and those in which $n$ is 1 (preferably at the 2- or 3-position) and $m$ is 0. The most preferred compounds, when X is —CO—, are those in which Y is a methyl group or a chlorine atom, $n$ is 1, and $m$ is 0 and, when X is —CHOH—, are those in which Y is a chlorine atom, $n$ is 1, and $m$ is 0.

Generally, the compounds used in the present invention are applied to the tobacco plants during the topping stage, and are usually applied during the period of about 1 to 7 days before to about 1 to 7 days after topping, and preferably on the same day as topping. The compounds can be applied in any amount which will give the desired degree of control of sucker growth, without significantly adversely affecting the growth of the tobacco plants. Typical rates of application will be from about 0.5 to about 20 pounds per acre, and preferably about 1 to about 10 pounds per acre.

The compounds of the invention can be applied to the growth medium or to plants to be treated either by itself or, as is generally done, as a component in a agricultural composition or formulation which also comprises an agronomically acceptable carrier. By agronomically acceptable carrier is meant any substance which can be used to dissolve, disperse, or diffuse a compound in the composition without impairing the effectiveness of the compound and which by itself has no detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, or flowable emulsion concentrates. In such formulations, the compounds are extended with a liquid or solid carrier and, when desired, suitable surfactants are incorporated.

It is usually desirable, particularly in post-emergence applications, to include adjuvants, such as wetting agents, spreading agents, dispersing agents, stickers, adhesives, and the like, in accordance with agricultural practice. Examples of adjuvants which are commonly used in the art can be found in the John W. McCutcheon, Inc. publication "Detergents and Emulsifiers Annual."

The compounds of this invention can be dissolved in any appropriate solvent. Examples of solvents which are useful in the practice of this invention include alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% by weight with a preferred range being about 25% to about 75%.

For the preparation of emulsifiable concentrates, the compounds can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols, such as t-octylphenol, or long-chain alcohols, and their phosphoric acid esters, mercaptans, carboxylic acids, and reactive amines and partially esterified polyhydric alcohols. Solvents, soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water soluble salt of a polyacrylic acid. The concentration of the active ingredient in emulsifiable concentrates is usually about 10% to 60% by weight and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98% by weight, preferably about 40% to 75%. A dispersing agent can constitute about 0.5% to about 3% of the composition, and a wetting agent can constitute from about 0.1% to about 5% of the composition.

The compounds of the invention can be applied as sprays by methods commonly employed, such as conventional high-gallonage hydraulic sprays, low gallonge sprays, air-blast sprays and aerial sprays. For low volume applications a solution of the compound is usually used. The dilution and rate of application will usually depend upon such factors as the type of equipment employed, the method of application, and the area to be treated.

For some applications, it may be desirable to use one or more other tobacco sucker control agents along with compounds of the invention. Examples of other tobacco sucker control agents which can be combined or applied sequentially with the compounds of the invention to provide additional advantages and effectiveness include maleic hydrazide, N-2-pentyl-3,4-dimethyl-2,6-dinitroaniline, dodecyl dimethyl ammonium acetate, 5,6-dihydro-2,3-diphenyl-1,4-oxathiin, N-n-butyl-N-ethyl-2,6-dinitro-4-trifluoromethylaniline, $C_6$ to $C_{12}$ fatty alcohols, and mixtures of such alcohols, and the like. When mixtures of tobacco sucker control agents are employed, the relative proportions which are used can be varied greatly depending on the degree of control desired and particular conditions which may be present. The compounds of the invention can also be combined when appropriate with other pesticides useful in tobacco, including insecticides, fungicides, viricides, herbicides, and the like, to simplify application of these materials.

The compounds of the invention or their precursors are either known compounds or ca be prepared by conventional synthetic methods. For example, the benzophenones of the invention can be prepared by a Friedal-Crafts acylation of an appropriately substituted benzene with a benzoic acid, acid chloride, or anhydride in the presence of a Lewis acid catalyst, such as aluminum chloride, ferric chloride, zinc chloride, stannic chloride, titanium chloride, or the like. The acylation reaction is generally run at a temperature of about 0° to about 200° C, optionally in an inert solvent such as carbon disulfide, 1,2-dichloroethane, chlorobenzene, nitrobenzene, or the like. When a benzoic acid is used as the acylating agent, polyphosphoric acid or liquid hydrogen fluoride are also useful solvents. The benzhydrols of the invention can be prepared, for example, by the reduction of the corresponding benzophenone, or by reacting a substituted benzaldehyde with an aryl Grignard reagent. Reduction of benzophenones is generally carried out using a reducing system such as sodium borohydride in isopropanol, aluminium isopropoxide in isopropanol, zinc/sodium hydroxide in 95% ethanol, formaldehyde/sodium hydroxide in methanol, at a temperature of about 0° to about 100° C. The Grignard reaction is generally carried out in an inert solvent such as diethyl ether, glyme, tetrahydrofuran or the like, at a temperature of about 0 to about 100° C. Other conventional methods and modifications of these methods can also be employed in preparing compounds of the invention.

The following examples will further illustrate this invention, but are not intended to limit it in any way. All parts and percentages are by weight and all temperatures in degrees Centrigrade unless otherwise noted. Example A shows a typical procedure used in preparing the benzophenones of the invention and Example B shows a typical procedure used in preparing the benzhydrols of the invention.

EXAMPLE A

Preparation of 3-chlorobenzophenone

To a refluxing solution containing 43.9g (0.25 mole) of 3-chlorobenzoyl chloride in 120 ml. of dry benzene is added 30.0 g. (0.225 mole) of anhydrous aluminum chloride in several portions over a period of 10 minutes. When the reaction is complete, as indicated by vapor phase chromatographic (vpc) techniques, the mixture is cooled to 25° and diluted with ether. Extraction with dilute base is followed by thorough drying (magnesium sulfate) and concentration in vacuo. Final purification is effected by recrystallization from ether-hexane to afford 13.7g (0.06 mole) of 3-chlorobenzophenone, m.p. 84°–85°.

EXAMPLE B

Preparation of 2-chlorobenzhydrol

A mixture containing 15.0 g (0.0692 mole) of 2-chlorobenzophenone, 4.1 g (0.1094 mole) of sodium borohydride, and 200 ml of anhydrous isopropanol is heated to reflux and maintained at reflux until the reaction is complete (2.0 hours), as indicated by vpc techniques. The solvent is removed in vacuo, whereupon the residue is diluted with ether, washed with a dilute hydrochloric acid solution and with water until neutral, dried (magnesium sulfate), and concentrated in vacuo. Recrystallization of the resulting residue from petroleum ether affords 11.5 g (0.0526 mole) of 2-chlorobenzhydrol, m.p. 61-63°.

The following benzophenones and benzhydrols are representative of compounds which are useful in the practice of the present invention:

3-bromobenzophenone
3,3'-dibromobenzophenone
4-ethylbenzophenone
3,3'-dichlorobenzophenone
2-cyanobenzophenone
4-carbamoylbenzophenone
2-methylcarbamoylbenzophenone
2-chloro-3'-methylthiobenzophenone
2,4'-dichloro-4-nitrobenzophenone
4-methoxy-3-methyl-3'-trifluoromethylbenzophenone
4-methoxy-3-methylbenzophenone
3-hydroxybenzophenone
3-iodobenzophenone
2-nitrobenzophenone
4-carbethoxy-3'-methylbenzophenone
2,4,6-trichlorobenzophenone
3,5-dichloro-3'-methylbenzophenone
3-n-butoxy-3'-chlorobenzophenone
3-bromo-3'-chlorobenzophenone
3-bromo-4'-chlorobenzophenone 2-n-propyl-3'-chlorobenzophenone
3,3'-dichloro-2-nitrobenzophenone
3-chloro-3'-methylbenzophenone
4-ethoxybenzophenone
3-diethylcarbamoylbenzophenone
2-hydroxy-3',5'-dichlorobenzophenone
3-trifluoromethylbenzophenone
3-chloro-4'-trifluoromethylbenzophenone
2,4-dichloro-6-fluorobenzophenone
3,4-dimethoxybenzophenone
3,3'-bis(trifluoromethyl)benzophenone
2,4'-dimethoxybenzophenone
3-carboxy-2'-chlorobenzophenone
4-methoxy-2'-nitrobenzophenone
3-nitro-2'-(trifluoromethyl)benzophenone
2-methoxy-3'-(trifluoromethyl)benzophenone
4-methoxy-2'-(trifluoromethyl)benzophenone
3-nitro-4'-methoxybenzophenone
and each of the corresponding benzhydrols.

EXAMPLES 1 to 17

Control of Tobacco Suckers

This example shows the activity of benzophenones and benzhydrols in inhibiting the growth of tobacco suckers when compared to an untreated control. The following test procedure is employed. Tobacco plants growing in the greenhouse are topped at early flowering stage, to induce incresed growth of the remaining leaves by preventing development of the seed head and reducing the number of leaves on the plant. A few days after the topping, one hundred-fifty milligrams of each compound is topically sprayed in 20 ml of acetone:water solution (85:15). The coarse spray, applied with no more than 20 lbs. pressure, is directed to the center of the plant so that it runs down the stalk and makes contact with each sucker. A continual observation regarding phytotoxicity and degree of sucker killing is recorded. Final sucker control is determined three to four weeks after treatment by removing suckers from each plant and weighing them.

Table I lists typical compounds tested by structure and Table II summarizes typical results of the evaluations of these compounds. The reduction in weight of tobacco suckers is the ratio of the weight of suckers on the treated plants to the weight of suckers on untreated control plants. Phytotoxicity ratings are based on a 0 to 5 scale, in which 0 represents no injury and 5 represents complete kill.

TABLE I

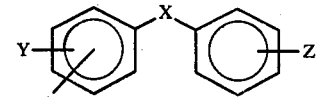

| Example No. | X | Y | Y' | Z |
|---|---|---|---|---|
| 1 | CO | 2-CH₃ | H | H |
| 2 | CO | 3-CH₃ | H | H |
| 3 | CO | 4-CH₃ | H | H |
| 4 | CO | 2-Cl | H | H |
| 5 | CO | 3-Cl | H | H |
| 6 | CO | 4-Cl | H | H |
| 7 | CHOH | 2-Cl | H | H |
| 8 | CHOH | 3-Cl | H | H |
| 9 | CHOH | 4-Cl | H | H |
| 10 | CHOH | 2-CH₃ | H | H |
| 11 | CHOH | 3-CH₃ | H | H |
| 12 | CHOH | 4-CH₃ | H | H |
| 13 | CHOH | H | H | H |
| 14 | CO | 3-CH₃ | 4-OCH₃ | 3-CH₃ |
| 15 | CO | 3-CH₃ | 4-OCH₃ | 2-Cl |
| 16 | CO | 3-CH₃ | 4-OCH₃ | 3-Cl |

TABLE I-continued

| Example No. | X | Y | Y' | Z |
|---|---|---|---|---|
| 17 | CO | 3-CH₃ | 4-OCH₃ | 4-Cl |

TABLE II

| | Control of Tobacco Sucker Growth | | |
|---|---|---|---|
| Compound of Example No. | Rate (mg/plant) | % Reduction in Sucker Weight* | Phytotoxicity |
| 1 | 150 | 53 | 0 |
| 2 | 150 | 38 | 0 |
| 3 | 150 | 12 | 0 |
| 4 | 150 | 55 | 0 |
| 5 | 150 | 11 | 0 |
| 6 | 150 | 26 | 0 |
| 7 | 150 | 92 | 0 |
| 8 | 150 | 89 | 0 |
| 9 | 150 | 24 | 1.5 |
| 10 | 150 | 17 | 0 |
| 11 | 150 | 38 | 0 |
| 12 | 150 | 50 | 0 |
| 13 | 150 | 35 | 0 |
| 13 | 300 | 81 | 0 |
| 14 | 150 | 81 | 0 |
| 15 | 150 | 72 | 0 |
| 15 | 150 | 62 | 0 |
| 16 | 150 | 0 | 0 |
| 16 | 150 | 63 | 0 |
| 17 | 150 | 63.5 | 0 |
| 17 | 150 | 56 | 0 |

*Examples 1 to 6 evaluated 25 days after treatment; Examples 7 to 13 evaluated 28 days after treatment; Examples 14 to 17 evaluated 21 days after treatment.

EXAMPLE 18

Emulsifiable Concentrate Formulations

The following example shows typical emulsifiable concentrate formulations of a compound for use in practicing the invention.

| Formulation I | |
|---|---|
| 2-chlorobenzhydrol | 27% (by weight) |
| octylphenoxypolyethoxyethanol (7.5 mol ethylene oxide) | 23% |
| water | 50% |
| Formulation II | |
| 2-methylbenzophenone | 50% |
| C₈-C₁₀ fatty alcohol blend (Alfol 810) | 33% |
| octylphenoxypolyethoxyethanol (7.5 mol ethylene oxide) monohydrogen and dihydrogen phosphate esters | 17% |

It is to be understood that changes and variations may be made without departing from the spirit and scope of the invention as defined by the appended claims.

I claim:

1. A method for controlling the growth of suckers in growing tobacco plants which comprises applying to the plants an effective aount of a compound of the formula

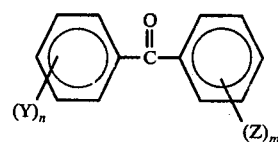

wherein each Y and each Z independently is a halogen atom, a ($C_1$-$C_8$) alkyl group, a trifluoromethyl group, a ($C_1$-$C_4$) alkoxy group, a hydroxy group, a nitro group or a ($C_1$-$C_4$) alkylthio group, $m$ is 0, 1, or 2, and $n$ is 0, 1, 2, or 3.

2. The method of claim 1 wherein $m$ is 0.

3. The method of claim 2 wherein Y is a halogen atom or an alkyl group and $n$ is 1.

4. The method of claim 2 wherein Y is a chlorine atom.

5. The method of claim 2 wherein Y is a methyl group.

6. The method of claim 1 wherein the compound is applied at a rate of about 0.5 to about 20 pounds per acre.

* * * * *